(12) United States Patent
Tsugane et al.

(10) Patent No.: US 10,201,493 B2
(45) Date of Patent: Feb. 12, 2019

(54) METHOD OF REDUCING ORAL BIOFILM

(71) Applicant: LOTTE CO., LTD., Tokyo (JP)

(72) Inventors: Takanori Tsugane, Saitama (JP); Shota Mohri, Saitama (JP); Yoji Saeki, Saitama (JP)

(73) Assignee: LOTTE CO., LTD., Tokyo (JP)

( * ) Notice: Subject to any disclaimer, the term of this patent is extended or adjusted under 35 U.S.C. 154(b) by 105 days.

(21) Appl. No.: 15/453,355

(22) Filed: Mar. 8, 2017

(65) Prior Publication Data

US 2017/0181962 A1    Jun. 29, 2017

Related U.S. Application Data

(62) Division of application No. 14/343,418, filed as application No. PCT/JP2012/005662 on Sep. 6, 2012, now abandoned.

(30) Foreign Application Priority Data

Sep. 8, 2011   (JP) ................................. 2011-196315

(51) Int. Cl.
| | |
|---|---|
| *A61K 36/31* | (2006.01) |
| *A61K 8/97* | (2017.01) |
| *A23L 2/02* | (2006.01) |
| *A23L 2/52* | (2006.01) |
| *A61Q 11/00* | (2006.01) |
| *A23G 3/48* | (2006.01) |
| *A23G 4/06* | (2006.01) |
| *A61K 36/11* | (2006.01) |
| *A61K 36/185* | (2006.01) |
| *A61K 36/25* | (2006.01) |
| *A23L 33/105* | (2016.01) |
| *A61K 8/02* | (2006.01) |
| *A61K 9/00* | (2006.01) |
| *A61K 9/68* | (2006.01) |
| *A61K 9/20* | (2006.01) |

(52) U.S. Cl.
CPC ................. *A61K 8/97* (2013.01); *A23G 3/48* (2013.01); *A23G 4/068* (2013.01); *A23L 2/02* (2013.01); *A23L 2/52* (2013.01); *A23L 33/105* (2016.08); *A61K 8/0204* (2013.01); *A61K 8/0216* (2013.01); *A61K 9/007* (2013.01); *A61K 9/0056* (2013.01); *A61K 9/0058* (2013.01); *A61K 9/0095* (2013.01); *A61K 9/20* (2013.01); *A61K 36/11* (2013.01); *A61K 36/185* (2013.01); *A61K 36/25* (2013.01); *A61K 36/31* (2013.01); *A61Q 11/00* (2013.01); *A23V 2002/00* (2013.01); *A61K 2236/33* (2013.01); *A61K 2236/331* (2013.01); *A61K 2800/92* (2013.01)

(58) Field of Classification Search
CPC ...................................................... A61K 36/31
USPC ........................................................ 424/755
See application file for complete search history.

(56) References Cited

U.S. PATENT DOCUMENTS

| | | | |
|---|---|---|---|
| 7,879,375 B1 | 2/2011 | Javor | |
| 2003/0064097 A1 | 4/2003 | Patel et al. | |
| 2007/0178054 A1* | 8/2007 | Srinivasa ................. | A61K 8/21 424/50 |
| 2010/0029557 A1 | 2/2010 | Sigh et al. | |
| 2010/0136179 A1 | 6/2010 | Mochizuki et al. | |
| 2010/0173024 A1 | 7/2010 | McDaniel | |
| 2011/0189348 A1 | 8/2011 | Inoue et al. | |
| 2011/0278492 A1 | 11/2011 | Arai et al. | |
| 2012/0020896 A1* | 1/2012 | Trivedi ..................... | A61K 8/37 424/49 |
| 2012/0136138 A1 | 5/2012 | Kegasa et al. | |
| 2013/0022730 A1* | 1/2013 | Obata .................... | A23L 1/0534 426/590 |
| 2013/0089506 A1* | 4/2013 | Wang ....................... | A61K 8/97 424/58 |
| 2013/0189202 A1* | 7/2013 | Tsugane ................... | A23G 3/48 424/58 |
| 2013/0344010 A1* | 12/2013 | Pompejus ................ | A61K 8/99 424/50 |

FOREIGN PATENT DOCUMENTS

| | | |
|---|---|---|
| CN | 1552723 A | 12/2004 |
| CN | 1931212 A | 3/2007 |
| CN | 101244113 A | 8/2008 |
| JP | 62-265960 A | 11/1987 |
| JP | 02-207023 A | 8/1990 |
| JP | 03-017010 A | 1/1991 |
| JP | 06-329544 A | 11/1994 |
| JP | 10-259136 A | 9/1998 |
| JP | 11-158011 A | 6/1999 |
| JP | 11-158053 A | 6/1999 |
| JP | 2000-319120 A | 11/2000 |

(Continued)

OTHER PUBLICATIONS

Kimura, Hiroshi., "Cervical Actinomycosis Due to *Actinomyces naeslundii*", Journal of Otolaryngology of Japan, vol. 114, No. 7, pp. 620-623, 2011.

Matsubara, S., et al., "Promoters of In Vitro Pollen Germination of Radish and *Brassica campestris*", J. Japan Soc. Hort. Sci. 68(2), pp. 421-427, 1999.

Office Action dated Mar. 26, 2015, in Chinese Patent Application No. 201280043403.3.

International Preliminary Report on Patentability from International Application No. PCT/JP2012/005662, dated Mar. 20, 2014.

Office Action dated Oct. 17, 2018, in Korean Patent Application No. 10-2014-7009143.

*Primary Examiner* — Christopher R Tate

(74) *Attorney, Agent, or Firm* — Shapiro, Gabor and Rosenberger, PLLC

(57) ABSTRACT

An oral composition having a biofilm formation inhibitory action is provided. An oral composition, comprising a plant extract which is a hot water extract of Japanese mustard spinach, potherb mustard, mibuna, hot radish, cress, ostrich fern, Japanese angelica tree, or ice plant.

17 Claims, 1 Drawing Sheet

(56) References Cited

FOREIGN PATENT DOCUMENTS

| | | |
|---|---|---|
| JP | 2003-113106 A | 4/2003 |
| JP | 2003-238987 | 8/2003 |
| JP | 2004-115410 A | 4/2004 |
| JP | 2005-281272 A | 10/2005 |
| JP | 2007-099638 A | 4/2007 |
| JP | 2007-169246 A | 7/2007 |
| JP | 2008-517052 A | 5/2008 |
| JP | 2008-174542 A | 7/2008 |
| JP | 2011-121919 A | 6/2011 |
| JP | 2011-160798 A | 8/2011 |
| JP | 2012-224568 A | 11/2012 |
| WO | WO 2007/037492 A1 | 4/2007 |
| WO | WO 2008/060112 A1 | 5/2008 |
| WO | WO 2012/096270 A1 | 7/2012 |

* cited by examiner

A. naeslundii BIOFILM FORMATION WITH ACID ADDITION AND BIOFILM
FORMATION INHIBITORY EFFECT BY A POTHERB MUSTARD EXTRACT DIFFERENCE IN THE BIOFILM FORMATION INHIBITORY ACTIVITY
BY THE EXTRACTANT OF HOT RADISH

METHOD OF REDUCING ORAL BIOFILM

TECHNICAL FIELD

The present invention relates to an oral composition having an inhibitory action by a plant extract on *Actinomyces naeslundii* (hereinafter referred to as "*A. naeslundii*") biofilm formation.

BACKGROUND ART

Microorganisms attached on the surface of an object do not exist independently, but form a biofilm together with other microorganisms in the characteristic structure. The biofilm, which appears to work in favor of the human as seen in the use of immobilized microorganisms, is conversely revealed to cause tooth decay and food contamination, and has been extensively studied in recent years.

The dental biofilm includes 700 species or more of bacteria and $10^8$ or more bacteria are present per 1 mg of the dental biofilm. Of these, *A. naeslundii* has been receiving much attention in recent years as a key microorganism required when the initial stage plaque (cariogenic plaque) proceeds to the late stage plaque (periodontal disease plaque).

In the conventional periodontal disease prevention, the mainstream idea was to sterilize periodontal disease bacteria such as *Porphyromonas gingivalis* (hereinafter referred to as "*P. gingivalis*") to inhibit the periodontal diseases. However, in reality, the periodontal disease foci are present with a biofilm deeply in the periodontal pocket, which prevents an antibacterial substance from permeation. Therefore, the conventional periodontal disease prevention fails to achieve an intended effect, and additionally always facing the risk of the resistant bacteria emergence. Thus, a safer and more effective prevention method has been in demand.

Also, mechanical removal such as brushing, and scaling, is believed to be the most effective method for inhibiting a biofilm, but it is difficult to practice suitable oral care using the current procedure for people having difficulties in such a mechanical control of dental biofilm such as the elderly in need of nursing care, whereby the development of biofilm removal procedures different from the convention procedures are in demand.

Short chain fatty acids (SCFA) such as butyric acid, are known to be present in a high concentration in the periodontal pocket and the dental plaque of periodontal disease patients, and the association thereof with the development and progress of the periodontal diseases became clear. In recent years, it was confirmed that acids such as SCFA produced by the periodontal disease bacteria such as *P. gingivalis* has a promoting effect on biofilm formation of *A. naeslundii*, and the studies on investigation of mechanism and pathogenic development control which targets this phenomenon are conducted (NIHON UNIVERSITY SCHOOL OF DENTISTRY, National Institute of Infectious Diseases, Japan).

In the present invention, with an attention on the influence by acids to the *A. naeslundii* biofilm formation, a substance, which is capable of inhibiting the biofilm formation depending on acids such as butyric acid thereby to inhibit the periodontal disease biofilm formation, was searched for, and a development of a novel periodontal disease biofilm inhibiting material with such substance was attempted.

An example of the literature regarding an oral composition exhibiting an antibacterial effect on the dental biofilm and an improvement effect on the gingivitis is PTL 1. PTL 1 discloses an oral composition containing (A) N-acylsarcosine or a salt thereof and (B) benzylisothiocyanate in a mass ratio (A)/(B) of 0.5 to 20, and also discloses that the oral composition has a good antibacterial effect on the dental biofilm causing the oral diseases and improvement effect on the gingivitis. However, PTL 1 does not disclose nor suggest any effects on the periodontal diseases.

CITATION LIST

Patent Literature

PTL 1: Japanese Patent Application Laid-Open No. 2008-174542

SUMMARY OF INVENTION

Technical Problem

Conventionally, in the methods for inhibiting the periodontal diseases which employ a certain antibacterial agent, the dental biofilm prevents the permeation of antibacterial agents and thus makes it difficult to achieve the intended periodontal disease inhibitory effects. Further, the use of antibacterial agents involves a high risk of resistant bacteria emergence, hence is not preferable. For these reason, controlling biofilm formed by *A. naeslundii*, which related to the initial stage of periodontitis is considered to be a periodontal disease prevention method which is safer and more effective than sterilizing the periodontal disease bacteria.

Solution to Problem

The present inventors conducted extensive studies and found that each of the plant extracts of potherb mustard, Japanese mustard spinach, hot radish and peppergrass belonging to the Brassicaceae family, Japanese angelica tree belonging to the Araliaceae family, and ice plant belonging to the Aizoaceae family has an inhibitory effect on the *A. naeslundii* biofilm formation induced by acid, whereby the present invention was accomplished.

The biofilm formation of *A. naeslundii* increases by the acid stimulation, but when 1000 ppm of the above plant is added to the culture system, the biofilm formation was found to be reduced to about 30%. At this time, some plant extracts did not affect the growth of *A. naeslundii*, suggesting that this biofilm formation inhibitory effect has a different mechanism from the antibacterial action.

*A. naeslundii* is a Gram-positive *bacillus* found in the sites of gingivitis and root surface caries and believed to be the pathogenic bacterium of the initial periodontal disease. Since *A. naeslundii* coaggregates with *Streptococcus* and the periodontal disease bacteria, it is considered to be a bacterium which is the key to the transition of bacterial flora to the periodontal plaque, which suggests that the control of *A. naeslundii* leads to the effective periodontal disease prevention.

The present inventors have validated that the biofilm formation was increased by the acids produced by the oral bacteria.

Advantageous Effects of Invention

The present invention provides a periodontal disease preventive agent with a new perspective, and is believed,

DESCRIPTION OF EMBODIMENTS

Figure 1:
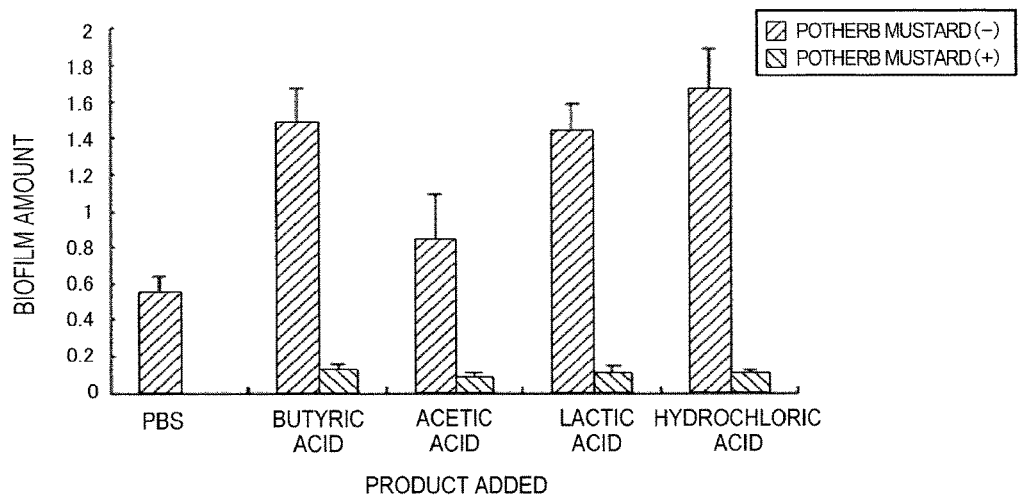
FIG. 1 is a graph showing the *A. naeslundii* biofilm formation by the acid addition.

The present invention is directed to prevent the periodontal diseases by inhibiting the periodontal disease biofilm formed by *A. naeslundii*, an initial stage periodontal disease bacterium, and based on the findings such a periodontal disease biofilm inhibitor in the extracts of a part of the Brassicaceae family plants such as potherb mustard, Japanese mustard spinach and hot radish; Japanese angelica tree; and ice plant.

Being unlike the conventional antibacterial agents used for periodontal disease bacteria, the present inhibitor inhibits the biofilm formation, which is the dwelling of periodontal disease bacteria, and is believed to be effective and safe.

The present inhibitor is also applicable to chewing gums and candies as a novel oral composition. More specifically, the present invention relates to an oral composition containing a plant extract, wherein the plant extract is a hot water extract of Japanese mustard spinach, potherb mustard, mibuna (*Brassica campestris* var, *laciniifolia*), hot radish, cress, ostrich fern, Japanese angelica tree, or ice plant.

Further, the present invention relates to an acid-induced biofilm formation inhibitor containing a plant extract, wherein the plant extract is a hot water extract of Japanese mustard spinach, potherb mustard, mibuna, hot radish, cress, ostrich fern, Japanese angelica tree, or ice plant.

Furthermore, the present invention relates to mouthwashes, toothpastes, inhalants, troches, and food products such as chewing gums, candies, and tablets, comprising an oral composition containing a plant extract, which is a hot water extract of Japanese mustard spinach, potherb mustard, mibuna, hot radish, cress, ostrich fern, Japanese angelica tree, or ice plant.

EXAMPLE

Example 1

(Extract Preparation)

Each of the plant samples was a commercially purchased product. After freeze-dried, 1 g of each of the plant samples was finely ground using a grinder, and extracted with 50 ml of water at 70° C. for 2 hours. The obtained extract was centrifuged at 3000 rpm for 10 minutes, the supernatant thereof was filtered and freeze-dried to be tested as a hot water extract of each plant.

Example 2

(Evaluation on the Biofilm Formation Inhibitory Activity)

1. Biofilm Formation

*A. naeslundii* ATCC19039 strain was anaerobically cultured in 5 ml of Brain Heart Infusion (BHI) liquid media at 37° C. for 10 hours. Then, the bacteria collected by the centrifugal separation at 3000 rpm for 10 minutes was treated with PBS to adjust to $OD_{550nm}=0.5$ and used as a test sample suspension.

The test of biofilm formation was carried out using a 96-well microplate. In each well, 60 μl of the biofilm formation inhibitory sample, 20 μl of butyric acid, 20 μl of a test sample suspension containing *A. naeslundii* and 100 μof Toripticase soy broth with 0.5% sucrose added thereto were added and incubated for 16 hours at 37° C. under the conditions of 5% $CO_2$.

2. Quantitative Determination of Biofilm

The supernatant after the above incubation was removed and each well was washed twice with PBS. After washing, a 0.25% safranine solution was added to each well, allowed to stand for 15 minutes. The excess safranine solution was removed from each well and each well was washed twice with PBS. After washing, ethanol was added to each well, the stained safranine was eluted with shaking for 30 minutes and the absorbance at 492 nm was measured using a microplate reader to determine the amount of formed biofilm.

The amount of formed biofilm was shown in terms of the percentage, the amount formed with no sample added being 100.

(Result)

1. Biofilm Formation Inhibitory Effect of Natural Product Extract

Extracts of various natural products were examined for the biofilm formation inhibitory activity in a butyric acid added system. Hot water extracts of various plants were prepared and measured for the biofilm formation inhibitory activities, and it was confirmed that when the hot water extract of Japanese mustard spinach, potherb mustard, mibuna, hot radish, cress, ostrich fern, Japanese angelica tree, or ice plant was added to the test system, the biofilm formation amount remained substantially unchanged in the system to which butyric acid was not added, whereas the biofilm formation amount was reduced by 50 to 90% in the system to which butyric acid was added. The effect was outstanding particularly in the hot water extracts of plants of the Brassicaceae family (Table 1).

Subsequently, the *A. naeslundii* biofilm formation was investigated for any increase by the addition of acids other than butyric acid, and a potherb mustard extract was investigated for the acid-induced biofilm formation inhibition. As a result, it is revealed that the *A. naeslundii* biofilm formation was increased even with the addition of other acids than butyric acid, such as acetic acid, lactic acid, and hydrochloric acid, and the potherb mustard extract inhibits the biofilms thereof (FIG. 1).

Figure 2:
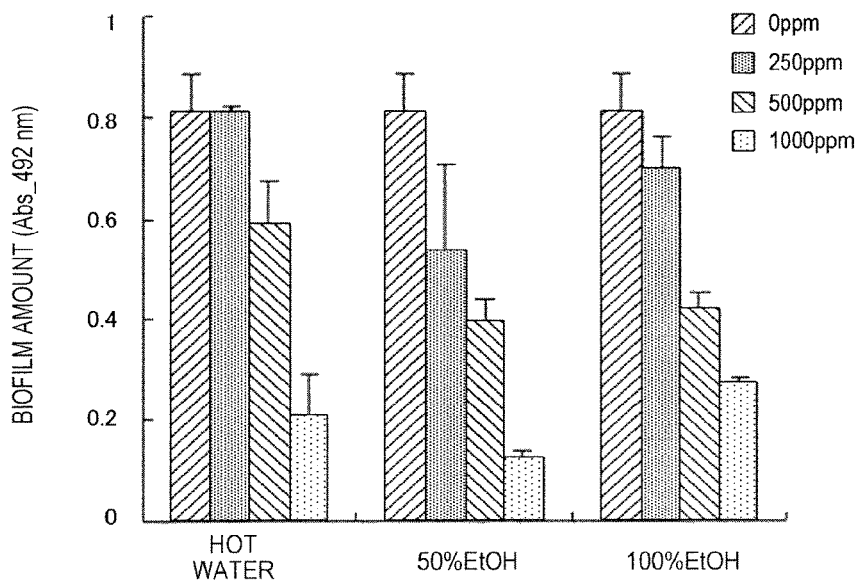
FIG. 2 is a graph showing the difference in the biofilm formation inhibitory activity by the extractant of a hot radish.

Hot radish whose activity was validated was extracted using different extractants (hot water, 50% ethanol, 100% ethanol), and each of which was examined for the biofilm formation inhibitory activity, and it was found that all the extract had the concentration dependent biofilm formation inhibitory activity (FIG. 2). These results suggest that the hot radish is most likely to contain both water soluble active substance and lipid soluble active substance.

To develop a periodontal disease preventive material which works by a mechanism different from the conventional materials, a butyric acid-induced biofilm formation inhibitory substance was developed focusing on the phenomenon in which the *A. naeslundii* biofilm formation was increased by butyric acid.

On the premise that the material is used for food products, the search was carried out mainly in the plants commonly eaten and remarkable activities were found in several kinds of plant extracts. These extracts did not notably inhibit the biofilm formation in the system to which butyric acid was not added but inhibited in the system to which butyric acid was added, indicating that the extracts were likely to affect only the system associated with butyric acid. In the present tests, the activity was found in the Brassicaceae family plants. But some of the Brassicaceae family plants do not exhibit the biofilm formation inhibitory activity. So, the effect was not common in all of the Brassicaceae family plants.

Also, the significant biofilm formation inhibitory activity was found in the extract of ice plant, an Aizoaceae family plant. Ice plant (scientific name: *Mesembryanthemum crystallinum*) is a salinity tolerant halophilous plant, native to Europe, western Asia and Africa, and can be hydroponically cultivated in a sodium chloride aqueous solution having a saline concentration substantially equivalent to the seawater. Ice plant is sold at the vegetable section of department stores and grocery stores in recent years and has been receiving attention. If additional values such as the periodontal disease biofilm prevention effect, were found, even more attention will be paid thereto.

The control of microorganisms and the conquer of infectious diseases using antibacterial agents, germicides, or the like, are the challenges against the resistant bacteria emergence, and the endless battles between novel antibiotics development and resistant bacteria emergence have been still ongoing at present. However, the biofilm formation inhibitory activity found in the plant hot water extracts obtained this time is verified only at the time of adding acids, and therefore, it is likely to be very safe in view of the resistant bacteria emergence.

Based on the results in this invention, investigation of the mechanism of the effect, identification of the active ingredient and effect tests on human will be carried out hopefully to develop a novel periodontal disease biofilm formation inhibitory material and apply such a material to oral care products.

Substances inhibiting the *A. naeslundii* biofilm formation induced by the addition of butyric acid were searched and it was found that the hot water extracts of 5 varieties belonging to the Brassicaceae plants such as Japanese mustard spinach and potherb mustard, and ice plant inhibited the biofilm formation by 50 to 90%. Further, it was suggested that the active ingredient of the Brassicaceae plants contains both of water soluble and lipid soluble substances.

TABLE 1

Biofilm formation inhibitory effect of hot water extracts of natural products

| | Sample | Family | Genus | Sample 500 ppm Butyric acid − | Sample 500 ppm Butyric acid + | Sample 1000 ppm Butyric acid − | Sample 1000 ppm Butyric acid + |
|---|---|---|---|---|---|---|---|
| | — | | | 100.0 | 100.0 | 100.0 | 100.0 |
| 1 | Beet | Chenopodiaceae | *Beta* | 87.3 | 104.5 | 132.0 | 96.4 |
| 2 | Swiss chard | Chenopodiaceae | *Beta* | 333.6 | 80.2 | 327.8 | 30.6 |
| 3 | Raw coffee bean | Rubiaceae | *Coffea* | 84.5 | 16.8 | 19.0 | 12.0 |
| 4 | Coffee bean | Rubiaceae | *Coffea* | 260.9 | 35.6 | 4.8 | 22.3 |
| 5 | Indian mulberry | Rubiaceae | *Morinda* | 231.3 | 93.6 | 584.8 | 92.3 |
| 6 | Japanese mustard spinach | Brassicaceae | *Brassica* | 537.7 | 93.2 | 87.9 | 6.8 |
| 7 | Potherb mustard | Brassicaceae | *Brassica* | 113.1 | 8.0 | 116.7 | 8.9 |
| 8 | Mibuna | Brassicaceae | *Brassica* | 94.1 | 13.2 | 138.1 | 33.8 |
| 9 | Turnip | Brassicaceae | *Brassica* | 455.8 | 77.7 | 367.0 | 71.4 |
| 10 | Broccoli | Brassicaceae | *Brassica* | 51.8 | 101.4 | 68.9 | 98.8 |
| 11 | Rape blossom | Brassicaceae | *Brassica* | 297.4 | 101.8 | 278.2 | 104.5 |
| 12 | Kakina leaf | Brassicaceae | *Brassica* | 156.7 | 115.4 | 325.7 | 115.8 |
| 13 | Wasabi leaf | Brassicaceae | *Brassica* | 86.7 | 110.9 | 45.6 | 118.9 |
| 14 | Watercress | Brassicaceae | *Nasturtium* | 44.2 | 50.9 | 7.9 | 26.8 |
| 15 | Rucola | Brassicaceae | *Arugula* | 11.8 | 30.1 | 7.8 | 38.0 |
| 16 | Red radish | Brassicaceae | *Raphanus* | 50.9 | 22.7 | 39.2 | 11.2 |
| 17 | Hot radish | Brassicaceae | *Raphanus* | 91.0 | 83.2 | 81.9 | 27.5 |
| 18 | Radish | Brassicaceae | *Raphanus* | 49.2 | 97.2 | 46.6 | 74.6 |
| 19 | Cress | Brassicaceae | *Lepidium* | 523.1 | 87.7 | 302.2 | 36.9 |
| 20 | Horse radish | Brassicaceae | *Wasabia* | 80.4 | 71.7 | 57.6 | 73.0 |
| 21 | Ostrich fern | Woodsiaceae | *Matteuccia* | 29.7 | 23.4 | 20.8 | 11.5 |
| 22 | Japanese angelica tree | Araliaceae | *Aralia* | 117.0 | 9.5 | 103.9 | 1.8 |
| 23 | Zucchini | Cucurbitaceae | *Cucurbita* | 337.9 | 86.4 | 329.9 | 91.9 |
| 24 | Pumpkin | Cucurbitaceae | *Cucurbita* | 63.3 | 129.7 | 70.1 | 140.6 |
| 25 | Cucumber | Cucurbitaceae | *Cucumis* | 316.3 | 82.7 | 313.3 | 82.6 |
| 26 | Melon cucumber | Cucurbitaceae | *Cucumis* | 291.8 | 87.8 | 327.3 | 90.0 |
| 27 | Okinawan yellow cucumber | Cucurbitaceae | *Cucumis* | 107.1 | 124.5 | 97.5 | 117.1 |
| 28 | Bitter melon | Cucurbitaceae | *Momordica* | 522.6 | 77.5 | 568.1 | 79.8 |
| 29 | Wax gourd | Cucurbitaceae | *Benincasa* | 134.5 | 96.7 | 117.1 | 95.3 |
| 30 | Chicory | Asteraceae | *Cichorium* | 175.8 | 103.7 | 315.3 | 103.6 |
| 31 | Gynura bicolor | Asteraceae | *Gynura* | 145.0 | 100.4 | 137.6 | 105.7 |
| 32 | Nigana | Asteraceae | *Ixeris* | 94.7 | 91.1 | 87.4 | 95.4 |
| 33 | Butterbur scape | Asteraceae | *Petasites* | 509.7 | 124.9 | 511.2 | 129.3 |
| 34 | W blueberry | Ericaceae | *Vaccinium* | 168.6 | 98.8 | 212.8 | 102.0 |
| 35 | Chinese wolfberry fruit | Solanaceae | *Lycium* | 187.7 | 87.6 | 476.1 | 84.6 |
| 36 | Sweet green pepper | Solanaceae | *Capsicum* | 137.1 | 73.6 | 544.3 | 64.8 |
| 37 | Manganji pepper | Solanaceae | *Capsicum* | 102.7 | 81.0 | 118.5 | 82.0 |
| 38 | Green pepper | Solanaceae | *Capsicum* | 129.9 | 91.4 | 221.1 | 83.7 |
| 39 | Green chili | Solanaceae | *Capsicum* | 64.9 | 87.3 | 37.3 | 84.1 |
| 40 | Jalapeno pepper | Solanaceae | *Capsicum* | 103.7 | 98.9 | 72.7 | 85.9 |
| 41 | Eggplant | Solanaceae | *Solanum* | 235.5 | 70.2 | 579.3 | 66.1 |
| 42 | Potato | Solanaceae | *Solanum* | 166.2 | 95.7 | 229.8 | 97.2 |

TABLE 1-continued

Biofilm formation inhibitory effect of hot water extracts of natural products

| | | | Sample 500 ppm Butyric acid | | Sample 1000 ppm Butyric acid | |
|---|---|---|---|---|---|---|
| Sample | Family | Genus | − | + | − | + |
| 43 Cherry tomato | Solanaceae | *Solanum* | 193.8 | 102.9 | 372.1 | 102.9 |
| 44 Mizunasu eggplant | Solanaceae | *Solanum* | 127.7 | 117.0 | 151.7 | 108.3 |
| 45 Tomato | Solanaceae | *Solanum* | 164.4 | 103.1 | 131.4 | 110.7 |
| 46 Beinasu eggplant | Solanaceae | *Solanum* | 217.5 | 106.2 | 259.0 | 111.4 |
| 47 Pepino | Solanaceae | *Solanum* | 93.7 | 81.7 | 109.8 | 55.4 |
| 48 Red onion | Alliaceae | *Allium* | 447.4 | 111.3 | 660.6 | 96.0 |
| 49 Ice plant | Aizoaceae | *Mesembryanthemum* | 504.8 | 34.2 | 213.7 | 11.0 |
| 50 Prune | Rosaceae | *Prunus* | 263.8 | 107.6 | 401.7 | 66.0 |
| 51 Apricot | Rosaceae | *Prunus* | 126.0 | 108.6 | 388.5 | 112.7 |
| 52 Cherry | Rosaceae | *Prunus* | 313.5 | 124.3 | 485.0 | 183.3 |
| 53 Kidney bean | Fabaceae | *Phaseolus* | 240.3 | 86.9 | 320.0 | 86.5 |
| 54 Red kidney bean | Fabaceae | *Phaseolus* | 66.2 | 122.8 | 55.7 | 103.3 |
| 55 Feijoada bean | Fabaceae | *Phaseolus* | 82.3 | 120.8 | 106.5 | 103.6 |
| 56 Black kidney bean | Fabaceae | *Phaseolus* | 122.8 | 104.2 | 162.7 | 115.1 |
| 57 White flower bean | Fabaceae | *Phaseolus* | 102.4 | 116.4 | 84.8 | 122.3 |
| 58 Red pea | Fabaceae | *Pisum* | 182.3 | 123.1 | 275.5 | 121.6 |
| 59 Mung bean | Fabaceae | *Vigna* | 70.6 | 95.5 | 45.9 | 37.9 |
| 60 Dainagon azuki bean | Fabaceae | *Vigna* | 87.1 | 96.5 | 69.5 | 48.2 |
| 61 Bean sprout | Fabaceae | *Vigna* | 99.5 | 97.3 | 106.1 | 100.8 |
| 62 Black-eyed pea | Fabaceae | *Vigna* | 132.2 | 110.9 | 103.3 | 114.2 |
| 63 Winged bean | Fabaceae | Psophocarpus | 72.1 | 89.0 | 131.4 | 88.4 |
| 64 Lentil bean | Fabaceae | *Lens* | 244.9 | 120.4 | 457.2 | 115.8 |
| 65 Asparagus | Liliaceae | Asparagus | 106.1 | 97.1 | 150.3 | 100.0 |
| 66 Dogtooth violet | Liliaceae | Erythronium | 168.7 | 81.7 | 240.7 | 65.7 |
| 67 Hosta montana | Liliaceae | *Hosta* | 229.7 | 100.0 | 325.4 | 98.2 |

Subsequently, a mouthwash, toothpaste, breath freshening spray, troche, chewing gum, candy, tablet candy, gummy jelly, and beverage, all containing the acid-induced biofilm formation inhibitor containing the plant extract of the present invention, were produced by a conventional method. The formulae are shown below.

However, the scope of the present invention is not limited thereto.

Example 3

A mouthwash was produced according to the following formulation.

| Ethanol | 2.0% by weight |
|---|---|
| Japanese mustard spinach extract | 1.0 |
| Flavor | 1.0 |
| Water | Balance |
| | 100.0 |

Example 4

A toothpaste was produced according to the following formulation.

| Calcium carbonate | 50.0% by weight |
|---|---|
| Glycerol | 19.0 |
| Mibuna extract | 1.0 |
| Carboxymethylcellulose | 2.0 |
| Sodium lauryl sulfate | 2.0 |
| Flavor | 1.0 |
| Saccharin | 0.1 |
| Chlorhexidine | 0.01 |
| Water | Balance |
| | 100.0 |

Example 5

A breath freshening spray was produced according to the following formulation.

| Ethanol | 10.0% by weight |
|---|---|
| Glycerol | 5.0 |
| Hot radish extract | 1.0 |
| Flavor | 0.05 |
| Coloring agent | 0.001 |
| Water | Balance |
| | 100.0 |

Example 6

A troche was produced according to the following formulation.

| Cress extract | 92.3% by weight |
|---|---|
| Gum Arabic | 6.0 |
| Flavor | 1.0 |
| Sodium monofluorophosphate | 0.7 |
| | 100.0 |

Example 7

A chewing gum was produced according to the following formulation.

| Gum base | 20.0% by weight |
|---|---|
| Xylitol | 54.7 |
| Maltose | 15.0 |
| Sorbitol | 9.3 |
| Flavor | 0.5 |
| Potherb mustard extract | 0.5 |
| | 100.0 |

Example 8

A candy was produced according to the following formulation.

| Sugar | 50.0% by weight |
|---|---|
| Reduced sugar syrup | 33.0 |
| Citric acid | 1.0 |
| Flavor | 0.2 |
| L-Menthol | 1.0 |
| Potherb mustard extract | 0.4 |
| Water | Balance |
| | 100.0 |

Example 9

A tablet candy was produced according to the following formulation.

| Sugar | 74.7% by weight |
|---|---|
| Lactose | 18.9 |
| Ice plant extract | 2.0 |
| Fatty acid sucrose ester | 0.15 |
| Water | 4.25 |
| | 100.0 |

Example 10

A gummy jelly was produced according to the following formulation.

| Gelatin | 60.0% by weight |
|---|---|
| Reduced sugar syrup | 32.4 |
| Japanese angelica tree extract | 0.5 |
| Vegetable oil and fat | 4.5 |
| Malic acid | 2.0 |
| Flavor | 0.5 |
| | 100.0 |

Example 11

A beverage was produced according to the following formulation.

| Orange juice | 30.0% by weight |
|---|---|
| Ostrich fern extract | 0.5 |
| Citric acid | 0.1 |
| Vitamin C | 0.04 |
| Flavor | 0.1 |
| Water | Balance |
| | 100.0 |

INDUSTRIAL APPLICABILITY

The oral composition of the present invention is a periodontal disease preventive agent with a new perspective which exhibits the acid-induced periodontal disease biofilm formation inhibitory action, different from the conventional antibacterial agents against periodontal disease bacteria. Consequently, the oral composition of the present invention is likely to render advantages of having a lower risk of resistant bacteria emergence, or the like, when compared with the existing antibacterial agents, and the like, and thus applicable to various products.

This application claims the priority from Japanese Patent Application No. 2011-196315, filed on Sep. 8, 2011, and the disclosure of which is hereby incorporated by reference as a part of the present application.

The invention claimed is:

1. A method of reducing an oral biofilm formed by *Actinomyces naeslundii* in a patient having *Actinomyces naeslundii* in his/her oral cavity, comprising orally administering to said patient an amount of a treatment composition sufficient to reduce the biofilm, wherein said treatment composition consists essentially of an extract of potherb mustard.

2. The method of claim 1, wherein said treatment composition is administered as a constituent of a mouthwash.

3. The method of claim 1, wherein said treatment composition is administered as a constituent of a toothpaste.

4. The method of claim 1, wherein said treatment composition is administered as a constituent of an inhalant.

5. The method of claim 1, wherein said treatment composition is administered as a constituent of a breath-freshening spray.

6. The method of claim 1, wherein said treatment composition is administered as a constituent of a troche.

7. The method of claim 1, wherein said treatment composition is administered as a constituent of a tablet.

8. The method of claim 1, wherein said treatment composition is administered as a constituent of a food product.

9. The method of claim 8, wherein said treatment composition is from about 0.4% to about 1.0% by weight of the food product.

10. The method of claim 8, wherein the food product is a chewing gum.

11. The method of claim 8, wherein the food product is a candy.

12. The method of claim 8, wherein the food product is a liquid.

13. The method of claim 1, wherein said extract is a hot water extract.

14. The method of claim 1, wherein said extract is an aqueous alcoholic extract.

15. The method of claim 1, wherein said extract is an alcoholic extract.

16. The method of claim 14, wherein the alcohol is ethanol.

17. The method of claim 15, wherein the alcohol is ethanol.

\* \* \* \* \*